(12) United States Patent
Grainger et al.

(10) Patent No.: US 8,940,917 B2
(45) Date of Patent: Jan. 27, 2015

(54) RUTHENIUM COMPLEXES COMPRISING PARACYCLOPHANE AND CARBONYL LIGANDS, AND THEIR USE AS CATALYST

(75) Inventors: Damian Mark Grainger, Cambridgeshire (GB); Hans Guenter Nedden, Cambridgeshire (GB); Stephen James Roseblade, Cambridgeshire (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/005,436

(22) PCT Filed: Mar. 16, 2012

(86) PCT No.: PCT/GB2012/050587
§ 371 (c)(1),
(2), (4) Date: Feb. 21, 2014

(87) PCT Pub. No.: WO2012/123761
PCT Pub. Date: Sep. 20, 2012

(65) Prior Publication Data
US 2014/0155642 A1  Jun. 5, 2014

(30) Foreign Application Priority Data
Mar. 17, 2011  (GB) .................................. 1104522.6

(51) Int. Cl.
*C07F 15/00* (2006.01)
*B01J 31/24* (2006.01)

(52) U.S. Cl.
CPC .......... *C07F 15/0053* (2013.01); *B01J 2231/60* (2013.01); *A01J 2531/0263* (2013.01); *C07F 15/0046* (2013.01); *B01J 31/2409* (2013.01); *B01J 2231/321* (2013.01); *B01J 2231/52* (2013.01); *B01J 2531/821* (2013.01)
USPC .......................................... 556/21; 556/136

(58) Field of Classification Search
CPC .............. C07F 15/0046; C07F 15/0053; B01J 31/2409; B01J 2231/321; B01J 2231/52; B01J 2231/60

USPC .................................................. 556/21, 136
See application file for complete search history.

(56) References Cited

FOREIGN PATENT DOCUMENTS

| | | |
|---|---|---|
| EP | 0 906 322 B1 | 4/1999 |
| EP | 1 633 762 B1 | 3/2006 |
| WO | 97/47632 A1 | 12/1997 |
| WO | 01/74829 A1 | 10/2001 |
| WO | 2004111065 A1 | 12/2004 |

OTHER PUBLICATIONS

Houpis et al., Organic Letters, vol. 7, No. 10, pp. 1947-1950 (2005).*
International Search Report, dated May 14, 2012, from corresponding PCT application.
Kunkely et al., "Photoluminescence of (phanephos) tricarbonylrhenium(I) chloride with phanephos=4,12-bis (diphenylphosphino)-[2,2]-paracyclophane", Inorganic Chemistry Communications, 2002, vol. 5, pp. 391-394.
Houpis et al., "Synthesis of PPAT Agonist via Asymmetric Hydrogenation of a Cinnamic Acid Derivative and Stereospecific Displacement of (S)-2-Chloropropionic Aci", Organic Letters, 2005, vol. 7, No. 10, pp. 1947-1950.
Gibson et al., "[2.2]Paracyclophane derivatives in asymmetric catalysis", Org. Biomol. Chem., 2003, vol. 1, pp. 1256-1269.
Abstract of Colton et al., "Carbonyl halides of the Group VIII transition metals. V. Halocarbonyl derivatives of ruthenium(III) and ruthenium(II)", Australian Journal of Chemistry, 1971, vol. 24, No. 5, pp. 903-909.
Abstract of Cheemala et al., "New Paracyclophane Phosphine for Highly Enantioselective Ruthenium-Catalyzed Hydrogenation of Prochiral Ketones", Synthesis, 2007, vol. 24, pp. 3877-3885.
GB Search Report, dated Jun. 17, 2011, from corresponding GB application.

* cited by examiner

*Primary Examiner* — Porfirio Nazario Gonzalez
(74) *Attorney, Agent, or Firm* — Young & Thompson

(57) ABSTRACT

The present invention relates to the ruthenium complexes comprising paracyclophane and carbonyl ligands, methods for the preparation thereof and uses of the complexes in isomerization, hydrogenation, transfer hydrogenation, hydroformylation and carbonylation reactions.

20 Claims, No Drawings

RUTHENIUM COMPLEXES COMPRISING PARACYCLOPHANE AND CARBONYL LIGANDS, AND THEIR USE AS CATALYST

The present invention relates to ruthenium complexes and, in particular, ruthenium complexes comprising paracyclophane and carbonyl ligands.

Paracyclophanes and in particular [2.2]-paracyclophane derivatives are established ligands for transition metal-catalysed asymmetric reactions (see for example, S. E. Gibson and J. D. Knight, *Org. Biomol. Chem.*, 2003, 1, 1256-1269). Of these, paracyclophane bis(phosphines) have attracted considerable attention because catalysts derived from them show high levels of activity and selectivity in a number of useful asymmetric transformations.

For example, WO 97/47632 describes paracyclophane bis(phosphine) ligands and rhodium (Rh), ruthenium (Ru), iridium (Ir) or palladium (Pd) catalysts derived therefrom for asymmetric hydrogenation, isomerization, hydroboration, cyclization, arylation, alkylation and amination reactions. The ligands described have the formula depicted below;

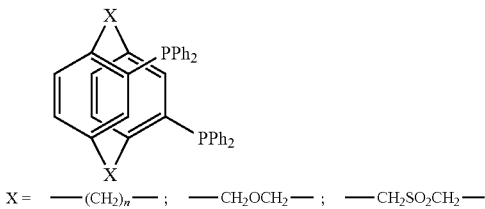

X = —(CH$_2$)$_n$— ;   —CH$_2$OCH$_2$— ;   —CH$_2$SO$_2$CH$_2$—

Where both X groups are identical, these ligands possess C$_2$ symmetry, that is they are chiral and have a C$_2$ axis of symmetry. For example, the C$_2$-symmetric [2.2] ligand where X=—(CH$_2$CH$_2$)—, known as PHANEPHOS, may be used in the asymmetric hydrogenation of ketones when comprising part of a Ru-diamine complex (see WO 01/74829).

Whereas the complexes described above are effective for many transformations there is still a need to improve the activity and selectivity of catalysts derived from them over a broader range of reactions and substrates.

Accordingly, the present invention provides a ruthenium complex of formula (1), (1b), (1c) or (1d):

[Ru Hal$_2$ L CO S]   (1a)

[Ru$_2$ Hal$_4$ L$_2$ (CO)$_2$]   (1b)

[Ru$_2$ Hal$_4$ L$_2$ CO]   (1c)

[Ru Hal$_2$ L (CO)$_2$]   (1d)

wherein:
Hal is a halogen ligand,
L is a substituted or unsubstituted paracyclophane ligand of formula (2):

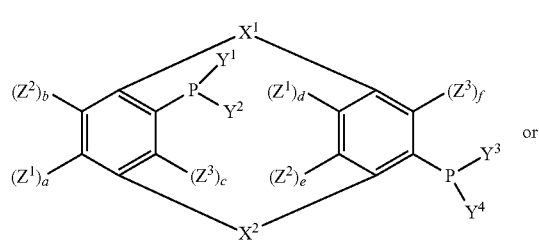

(2)

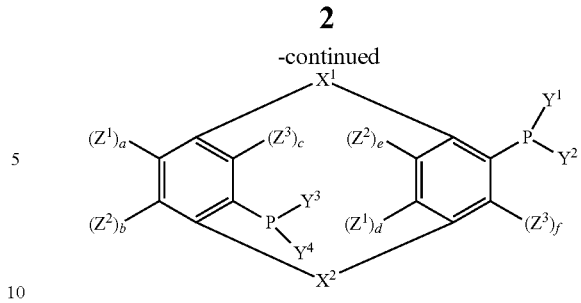

wherein X$^1$ and X$^2$ are linking groups comprising between 2 to 4 carbon atoms,
each Y$^1$, Y$^2$, Y$^3$ and Y$^4$ are independently selected from the group consisting of substituted or unsubstituted alkyl, substituted or unsubstituted cycloalkyl, substituted or unsubstituted aryl and substituted or unsubstituted heteroaryl,
each Z$^1$, Z$^2$ and Z$^3$ are the same or different and are substituting groups that optionally contain functional groups,
a, b, c, d, e and f are the integers 0 or 1 and a+b+c+d+e+f=0 to 6;
CO is a carbonyl ligand; and
S is a solvent ligand.

Hal is a halogen and may be selected from the group consisting of chlorine, bromine and iodine. In one embodiment, Hal is preferably chlorine.

L is a substituted or unsubstituted paracyclophane ligand of formula (2). Linking groups X$^1$ and X$^2$ provide links between the benzene rings of the paracyclophane structure that comprise between 2 and 4 carbon atoms. Hence X$^1$ and X$^2$ may be linear, branched or cyclic structures where the link is formed via 2, 3 or 4 carbon atoms. The links may, in addition to the carbon atoms, contain heteroatoms such as O, N or S (where the N atom may in turn be bonded to an alkyl group such as CH$_3$, C$_2$H$_5$, C$_3$H$_7$ or C$_4$H$_9$ or an aryl group, and the S atom may be bonded to an alkyl or aryl group or be part of an SO or SO$_2$ moiety) and/or the carbon atoms in the linking group may be substituted with a halide, e.g. one or more fluorine atoms. Hence linking groups X$^1$ and X$^2$ may independently be for example —(CH$_2$)$_{2-4}$—, —CH$_2$OCH$_2$—, —CH$_2$N(CH$_3$)CH$_2$—, —CH$_2$SO$_2$CH$_2$—, —C$_2$F$_4$— or ortho, meta or para —C$_6$H$_4$. Such modification of the linking group may be useful for adapting the substituted paracyclophane to different reaction conditions, e.g. solvents. Preferably the linking groups comprise —(C$_2$H$_4$)—, —(C$_3$H$_6$)— or —(C$_4$H$_8$)—. More preferably X$^1$ and X$^2$ are the same and most preferably X$^1$ and X$^2$ are both —(C$_2$H$_4$)—.

In one embodiment, the paracyclophane is a bis(phosphine) where each Y$^1$, Y$^2$, Y$^3$ and Y$^4$ may independently be straight chain or branched alkyl groups (e.g. C$_1$-C$_{20}$) such as methyl, ethyl, propyl, iso-propyl, butyl, iso-butyl, sec-butyl, tert-butyl, pentyl, hexyl, heptyl, octyl, nonyl, decyl, dodecyl, and stearyl, cycloalkyl groups (e.g. C$_3$-C$_{10}$) such as cyclopropyl, cyclobutyl, cyclopentyl, cyclohexyl or adamantyl, or aryl groups (e.g. C$_6$-C$_{20}$ aryl) such as phenyl, naphthyl or anthracyl. The alkyl groups may be optionally substituted with one or more substituents such as halide (Cl, Br, F or I) or alkoxy groups, e.g. methoxy, ethoxy or propoxy groups. The aryl groups may be optionally substituted with one or more substituents such as halide (Cl, Br, F or I), methyl, propyl (n- or i-), butyl (n-, i- or t-), trifluoromethyl, methoxy or dimethylamino groups. Suitable substituted aryl groups include 4-methyl phenyl, 3,5-dimethylphenyl, 4-methoxyphenyl, 4-methoxy-3,5-dimethylphenyl, 4-methoxy-3,5-diisopropyl phenyl, 4-methoxy-3,5-ditertbutylphenyl, 3,5-diisopropylphenyl, 3,5-ditertbutylphenyl, 4-dimethylamino-3,5-dimethylphenyl, 4-dimethylamino-3,5-diisopropylphenyl, 4-dimethylamino-3,5-ditertbutylphenyl and fluorenyl. Substituted or unsubstituted heteroaryl groups (e.g. substituted or unsubstituted $C_5$-$C_{20}$ heteroaryl groups) such as pyridyl or furanyl may also be used. In an alternative embodiment, $Y^1$ and $Y^2$ and/or $Y^3$ and $Y^4$ on each phosphorus atom may be linked so as to form a ring structure incorporating the phosphorus atom. In such an embodiment, preferably $Y^1$ and $Y^2$ and/or $Y^3$ and $Y^4$ are linked so as to provide each phosphorus atom in a 4- to 7-membered ring. Preferably, $Y^1$ and $Y^2$ and/or $Y^3$ and $Y^4$ are the same and are phenyl or substituted phenyl groups (e.g. dimethylphenyl groups, such as 3,5-dimethylphenyl or ditertbutylphenyl groups such as 3,5-ditertbutylphenyl).

When one or more of a, b, c, d, e and f are 1, substituting groups $Z^1$, $Z^2$ and $Z^3$ depending upon their number and position replace hydrogen atoms on one or both benzene rings of the paracyclophane (2). $Z^1$, $Z^2$ or $Z^3$ may independently be non-functional group-containing substituting groups such as branched or linear alkyl (e.g. $C_1$-$C_{30}$, preferably $C_1$-$C_{20}$, more preferably $C_1$-$C_{10}$ as described above for $Y^1$, $Y^2$, $Y^3$ and $Y^4$) or aryl (e.g. $C_6$-$C_{20}$-aryl, such as phenyl, naphthyl or anthracyl) or aralkyl or alkaryl, (e.g. benzyl, —$CH_2C_6H_5$). Such substituting groups may be effective in altering the physical, electronic and/or steric properties of the paracyclophane for example where the paracyclophane is used as part of a transition metal catalyst complex. Additionally or alternatively $Z^1$, $Z^2$ or $Z^3$ may be substituting groups that comprise one or more functional groups that may, if desired, be used to alter the electronic properties of the ligand, facilitate chiral resolution of the paracyclophane ligand or an intermediate thereof and/or covalently bond the paracyclophane ligand (or an intermediate thereof) and hence a catalyst derived therefrom, to a suitably reactive solid support. Hence substituting groups $Z^1$, $Z^2$ and $Z^3$ may independently optionally comprise one or more functional groups. Suitable functional groups include halide (Cl, Br, F or I), hydroxyl, alkoxy (i.e. —OR where e.g. R=alkyl $C_1$-$C_{30}$ as described above for $Y^1$, $Y^2$, $Y^3$ and $Y^4$), silyloxy (i.e. –$OSiR_3$ where e.g. R=alkyl $C_1$-$C_{30}$ as described above for $Y^1$, $Y^2$, $Y^3$ and $Y^4$), aralkyloxy (i.e. —O-alkyl-aryl e.g. —$OCH_2Ph$), carbonyl, carboxyl, anhydride, methacryl, epoxide, vinyl, nitrile, nitro, sulphate, sulphonyl, mercapto, sulphide amino, amine, imine, amide and imide. These functional groups may, where appropriate, be directly bonded to the benzene ring in the paracyclophane ligand or may be present in alkyl (e.g. $C_1$-$C_{30}$ as described above for $Y^1$, $Y^2$, $Y^3$ and $Y^4$), aryl or alkyl-aryl groups bonded to the benzene ring. In addition $Z^1$, $Z^2$ or $Z^3$ on one benzene ring in the paracyclophane structure may be the same or different from $Z^1$, $Z^2$ or $Z^3$ on the other benzene ring, i.e. $(Z^1)_a$, $(Z^2)_b$ and $(Z^3)_c$ may be the same or different from $(Z^1)_d$, $(Z^2)_e$, and $(Z^3)_f$.

Particularly preferred substituting groups are alkyl groups such as —$CH_3$ (Me), —$C(CH_3)_3$ (tBu), —$CH(CH_3)_2$ (iPr), aryl groups such as —$C_6H_5$ (Ph); fluoroalkyl groups e.g. of formula —$CxHyFz$ (in which x is 1 to 10, preferably 1 to 3; y is less than 2x, including 0; and z=1 to 2x+1), vinyl —CH=$CH_2$, iodide —I, nitrate —$NO_2$, imino e.g. —N=$CPh_2$, alkoxymethylene or alkoxy groups R'$OCH_2$— or R'O— (e.g. where R'=H, alkyl $C_1$-$C_{30}$, aryl, alkaryl or silyl, especially $CH_2Ph$, $CH_3$, tBu, iPr, $Si(tBu)Me_2$ or $Si(iPr)_3$); carbonyl XC(O)— (e.g. where X=H, halide, especially Cl, alkyl $C_1$-$C_{30}$, preferably $C_1$-$C_{10}$), carboxyl R"$O_2C$— (e.g. where R"=H, alkyl $C_1$-$C_{30}$, aryl or alkaryl such as $CH_3$, Ph—$CH_2$, tBu, iPr, preferably H); and amino R'R"N–, R'R"$NCH_2$— or R'R"NCO— (e.g. where R" and/or R"=H, alkyl, or alkaryl such as $CH_3$, $CH_2Ph$).

The substituting group on each benzene ring in the paracyclophane structure may be in an ortho ($Z^3$), meta ($Z^2$) and/or para ($Z^1$) position to the $P(Y^1Y^2)$ and $P(Y^3Y^4)$ groups.

When the substituent is at the para-position of the benzene ring it may enhance the electronic effects on the $P(Y^1Y^2)$ and $P(Y^3Y^4)$ groups and permits, by choice of suitable $Z^1$ substituents the possibility of electronic fine-tuning of the ligand to enhance its effect when part of a catalyst for different reactions and substrates. By careful choice of the $Z^2$ or particularly the $Z^3$ substituent in the ortho-position, the steric properties of the ligand may be altered to effect changes in catalyst selectivity. The substituting groups may also be used to alter the physical properties of the paracyclophane e.g. its stability in air, towards water, or its solubility in different solvents. Preferably the substituting group on each benzene ring in the paracyclophane is in the para ($Z^1$) position to the $P(Y^1Y^2)$ or $P(Y^3Y^4)$ groups.

At least one and up to six substituting groups may be present on the substituted paracyclophane (2). While each benzene ring in the paracyclophane structure may comprise three substituting groups, in one embodiment, each benzene ring comprises one or two substituting groups such that a+b+c+d+e+f=1 to 4, more preferably a+b+c+d+e+f=1 or 2. Most preferably each benzene ring comprises only one substituting group, i.e. a+b+c=1 and/or d+e+f=1 and particularly a and/or d=1.

In an alternative embodiment, a+b+c+d+e+f=0. In this instance, the paracyclophane (2) is unsubstituted and is known as a Phanephos ligand. In one embodiment, the paracyclophane (2) may be Phanephos or Xyl-Phanephos.

It will be understood by those skilled in the art that where one enantiomer of a paracyclophane of formula (2) is depicted, the other is included within the scope of the invention. Racemic mixtures are also included within the scope of the invention.

Paracyclophanes, suitable for use as ligands, include but are not restricted to the following:

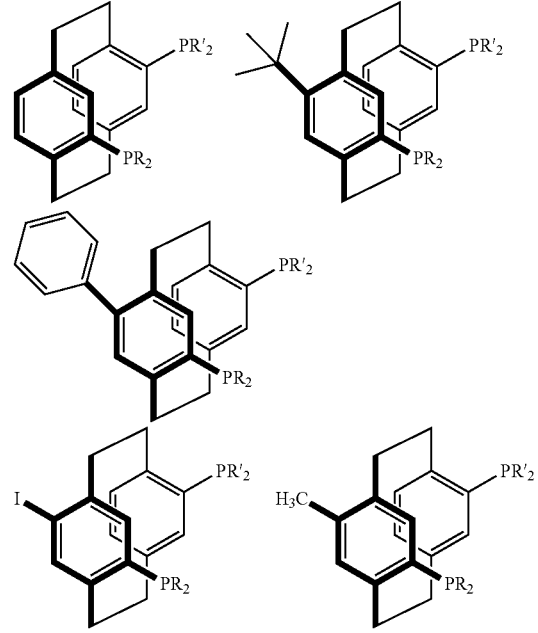

where

R=Ph, Tol, Xyl, MeO-Xyl, MeO—Ph, i-Pr, c-Hex, t-Bu, 3,5-tertBuphenyl

R"=Ph, Tol, Xyl, MeO-Xyl, MeO—Ph, i-Pr, c-Hex, t-Bu, 3,5-tertBuphenyl

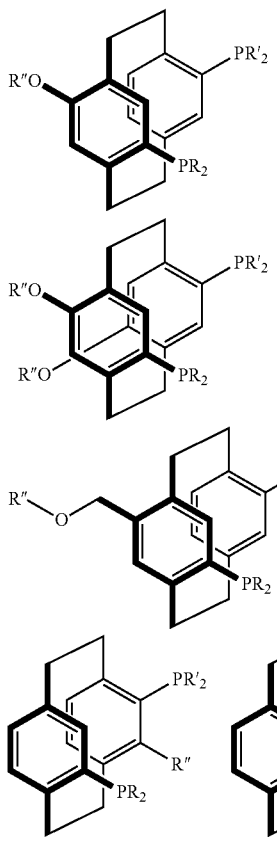

where

R,R' as above

R"=H, CH₂Ph, CH₃, t-Bu, i-Pr, Si(t-Bu)Me₂, Si(i-Pr)₃,

Methods for preparing the paracyclophane of formula (2) are described in EP906322, EP1633762 and Brown J, Rossen K, Knochel P, Synthesis, 2007, 24, 3877, which are incorporated herein by reference in their entirety for all purposes. The methods include electrophilic substitution (including Friedel Crafts alkylation and acylation reactions), nucleophilic substitution, and metallation-substitution reactions on a suitable paracyclophane intermediate. Alternatively the substituted paracyclophane may be constructed by coupling or dimerisation of suitably substituted and functional benzene ring units by e.g. thermal or photochemical means.

S is a solvent ligand and may be selected from the group consisting of amides (such as dimethylformamide or dimethylacetamide), N-heterocyles (e.g. pyridine), ketones (such as acetone, methylethyl ketone), alcohols (e.g. methanol, ethanol, 1-propanol or 2-propanol), esters (such as ethylformate or ethylacetate), aromatic solvents (e.g. benzene, toluene or a xylene), chlorinated alkanes (such as dichloromethane or chloroform), formic acid, dimethylsulfoxide and acetonitrile. In one preferred embodiment, the solvent ligand S is dimethylformamide (DMF).

Without wishing to be bound by theory, it is believed that the ligands form an octahedral or substantially octahedral molecular geometry around the ruthenium ions in the complexes of formulae (1a), (1b), (1c) and (1d). All isomers of the complexes therefore are included within the scope of the invention, such as those illustrated below. For clarity, the paracyclophane ligand L is represented as

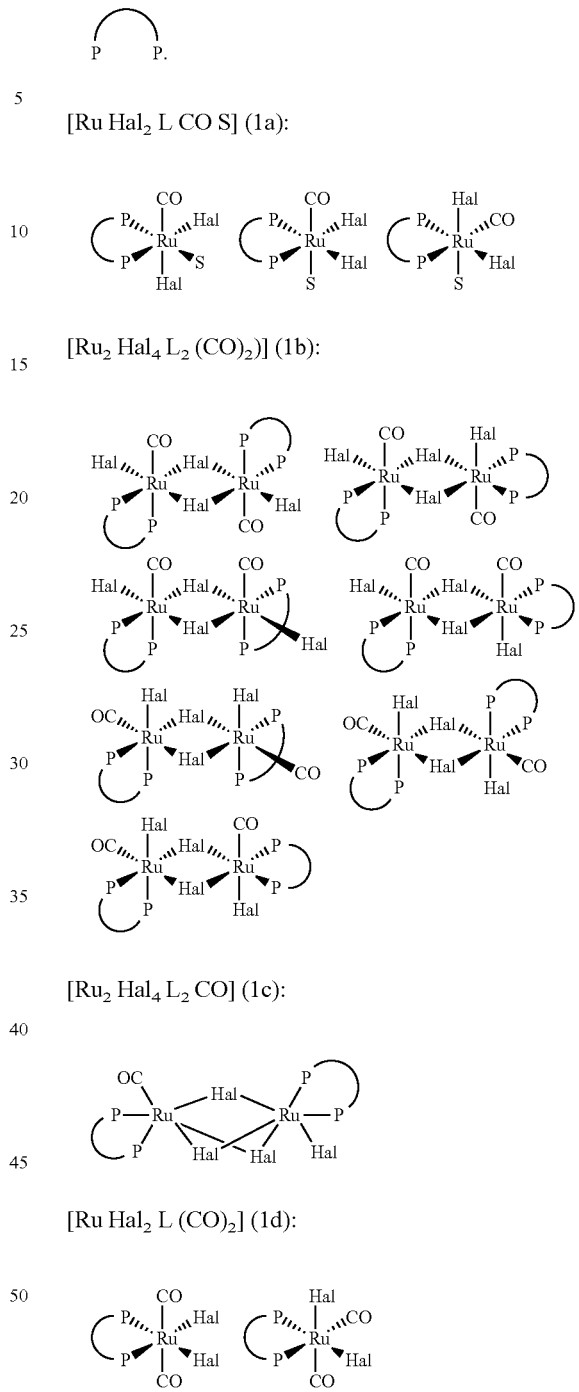

Without wishing to be bound by theory, it is believed that the complexes of formulae (1b) and (1c) are dimeric i.e. two ruthenium species, which may be the same or different, are linked together. In respect of (1b), the complex appears to have two bridging halogen atoms, whereas (1c) has three bridging halogen atoms. Complex (1c) also comprises a single CO ligand.

In one embodiment, the ruthenium complex is a complex of formula (1a). In a preferred embodiment, the complex of formula (1a) is a solid further comprising a co-crystallised solvent. In this embodiment, the ruthenium complex is preferably of the formula [Ru Hal₂ L CO S].S', wherein S is a solvent ligand, S' is the co-crystallised solvent, and S and S' are independently the same or different. S' may be selected from the group defined above with regard to the solvent ligand S. In one preferred embodiment, S and S' are the same. In one particularly preferred embodiment, S and S' are dimethylformamide (DMF).

In another embodiment, the ruthenium complex is a complex of formula (1b).

In yet another embodiment, the ruthenium complex is a complex of formula (1c).

In another embodiment, the ruthenium complex is a complex of formula (1d).

In one aspect, the present invention provides a method for the preparation of the ruthenium complex of formula (1a) as defined above, comprising the step of:

(a) reacting polymeric [Ru Hal$_2$ (CO)$_2$]$_n$, or [Ru Hal$_2$ (CO)$_3$]$_2$ with a paracyclophane ligand of formula (2) in a solvent S to form the complex of formula (1a); or (b) heating the complex of formula (1b) in a solvent S to form the complex of formula (1a); or (c) reacting [Ru (arene) Hal$_2$]$_2$ with a paracyclophane ligand of formula (2) in a solvent S to form the complex of formula (1a), wherein at least a portion of the solvent S decarbonylates to form CO.

In one embodiment, the polymeric [Ru Hal$_2$ (CO)$_2$], is polymeric [Ru Cl$_2$ (CO)$_2$]$_n$. In another embodiment, the [Ru Hal$_2$ (CO)$_3$]$_2$ is [Ru Cl$_2$ (CO)$_3$]$_2$. Polymeric [Ru Cl$_2$ (CO)$_2$]$_n$ and [Ru Cl$_2$ (CO)$_3$]$_2$ may be prepared according to Colton R., Farthing R., Aust, J. Chem., 1971, 24, 903, which is incorporated herein by reference in its entirety for all purposes.

Any suitable molar ratio of polymeric [Ru Hal$_2$ (CO)$_2$], or [Ru Hal$_2$ (CO)$_3$]$_2$: paracyclophane ligand (2) may be used, for example the molar ratio may be from about 2.5:1 to about 1:2.5, although it is generally preferred that the molar ratio is about 1:1. In this instance, as the number of moles of polymeric [Ru Hal$_2$ (CO)$_2$]$_n$ cannot be easily determined, the molar ratio is calculated as if the polymer consisted solely of monomeric species. If desired, the molar quantity of paracyclophane ligand (2) may be in slight excess to the molar quantity of polymeric [Ru Hal$_2$ (CO)$_2$]$_n$ or [Ru Hal$_2$ (CO)$_3$]$_2$. For example, the amount of paracyclophane ligand (2) in the reaction mixture may be calculated to provide a molar excess of up to about 10% over the amount required for the stoichiometric reaction.

The polymeric [Ru Hal$_2$ (CO)$_2$]$_n$ or [Ru Hal$_2$ (CO)$_3$]$_2$, paracyclophane ligand (2) and solvent S may be combined in any suitable order. In one embodiment, the [Ru Hal$_2$ (CO)$_2$]$_n$ or [Ru Hal$_2$ (CO)$_3$]$_2$ is combined with the paracyclophane (2) and the solvent S added. In another embodiment, the paracyclophane (2) is dissolved in the solvent S and the [Ru Hal$_2$ (CO)$_2$]$_n$ or [Ru Hal$_2$ (CO)$_3$]$_2$ added to the paracyclophane-containing solution. Any suitable quantity of the solvent S may be used, and the solvent S may be selected from the group defined above with regard to the solvent ligand S.

Alternatively, the complex of formula (1a) may be prepared by heating the complex of formula (1b) in the solvent S. Any suitable quantity of the solvent S may be utilised. In this instance, the dimeric complex (1b) dissociates and the vacant coordination site is occupied by a molecule of solvent S.

Alternatively, the complex of formula (1a) may be prepared by reacting [Ru (arene) Hal$_2$]$_2$ with the paracyclophane (2) in a solvent S, wherein at least a portion of the solvent S decarbonylates to form CO. The solvent S, therefore, acts as the source of the CO ligand. The solvent S may be selected from the group consisting of formic acid, formic acid esters (such as ethyl formate) and formic acid amides (such as dimethylformamide). Preferably, the solvent S is dimethylformamide.

In respect of preparing the complex (1a) by the method of step (c), the reaction may be heated at a temperature such that at least a portion of the solvent S decarbonylates to generate CO in situ. When the solvent S is DMF, the temperature may be selected from the range of about 110° C. to about ≤153° C. (i.e. the boiling point of the solvent). In one embodiment, the temperature may be selected from the range of about 110° C. to about 130° C., for example, about 110° C. to about 120° C. The time for which the reaction is conducted is not significant provided the reaction is conducted for a period of time sufficient for the solvent S to decarbonylate and to allow least some of the generated CO to coordinate to the ruthenium ion.

The molar ratio of the ruthenium starting material:paracyclophane (2) is generally similar to step (a) above and the [Ru (arene) Hal$_2$]$_2$, paracyclophane ligand (2) and solvent S may be combined in any suitable order. The [Ru (arene) Hal$_2$]$_2$ may be [Ru (benzene) Hal$_2$]$_2$ or [Ru (toluene) Hal$_2$]$_2$, preferably Ru (benzene) Cl$_2$]$_2$.

Regardless of whether the complex of formula (1a) is prepared by the method of step (a), step (b) or step (c), the reaction mixture is preferably heated (as necessary) and optionally stirred for a suitable period of time at a temperature less than the boiling point of the solvent S. Optionally, during the course of the reaction, small quantities of the solvent S and released carbon monoxide may be stripped from the reaction mixture. If desired, the progress of the reaction may be monitored by assaying samples of the reaction mixture by NMR.

On completion of the reaction, the solution of the complex (1a) in the solvent S may be used directly, if the application requires or tolerates such a solvent. Alternatively, the solvent S may be evaporated under reduced pressure and/or elevated temperature, and the complex (1a) dried. Drying may be performed using known methods, for example, at temperatures in the range of about 10-80° C. and preferably about 20-70° C. under about 1-30 mbar vacuum for about 30 minutes to about 5 days.

If desired, the complex of formula (1a) may be crystallized/recrystallized one or more times (e.g. 1, 2 or 3 times) from a suitable combination of solvents. For example, the complex (1a) may be dissolved in one or more solvents comprising a chlorinated alkane (such as dichloromethane (DCM)), an ether (for example, methyl tert-butyl ether (MTBE)) or an aromatic solvent (such as toluene) and precipitated using an anti-solvent comprising an alkane (such as hexane). As used herein, the term anti-solvent refers to a solvent in which the desired product (i.e., the product being crystallized or recrystallized) is insoluble or essentially insoluble; the function of an anti-solvent thus is to reduce the solubility of the product in the solvent mixture and enhance the yield of precipitated crystals thereby recovered. The amount of anti-solvent employed preferably is sufficient to effect precipitation of at least the majority of the complex (1a) present in the reaction mixture. Suitable solvent/anti-solvent combinations include but are not limited to DCM/hexane, MTBE/hexane, MTBE/DCM/hexane. Alternatively or in addition, the complex (1a) may be crystallized/recrystallized from a combination of solvents in which the complex is soluble. Suitable solvents include aromatic solvents (such as toluene) and esters (for example ethyl acetate). A suitable combination of solvents includes toluene/ethyl acetate.

In yet another aspect, the present invention provides a method for the preparation of the ruthenium complex of formula (1b) as defined above, comprising the step of reacting polymeric [Ru (Hal)$_2$ CO (H$_2$O)]$_n$ with the paracyclophane ligand of formula (2) in a solvent mixture comprising at least one alcohol and chlorinated alkane to form the complex of formula (1b).

The polymeric [Ru (Hal)$_2$ CO (H$_2$O)$_n$] may be prepared according the procedure provided in Colton R., Farthing R., Aust, J. Chem., 1971, 24, 903. Preferably, the polymeric [Ru (Hal)$_2$ CO (H$_2$O)]$_n$ is polymeric [Ru Cl$_2$ CO (H$_2$O)].

The solvent is selected from at least one alcohol and chlorinated alkane. Examples of suitable alcohols and chlorinated alkanes are given above in respect of solvent S. In one embodiment, a preferred alcohol is methanol. In another embodiment, a preferred chlorinated alkane is DCM.

The polymeric [Ru (Hal)$_2$ CO (H$_2$O)]$_n$, paracyclophane (2) and solvents may be combined in any suitable order. In one embodiment, the polymeric [Ru (Hal)$_2$ CO (H$_2$O)]$_n$ may be dissolved in the alcohol and the paracyclophane (2) may be dissolved in the chlorinated alkane. The two solutions may then be combined and reacted to form the complex (1b). Any suitable quantities of solvent may be used provided the polymeric [Ru (Hal)$_2$ CO (H$_2$O)]$_n$ and paracyclophane (2) are sufficiently dissolved.

The molar ratio of the ruthenium starting material:paracyclophane ligand (2) is generally similar to that given above in respect of complex (1a). As the number of moles of [Ru (Hal)$_2$ CO (H$_2$O)]$_n$ cannot be easily determined, the molar ratio is calculated as if the polymer consisted solely of monomeric species. The direct use of the complex (1b) in the solvent mixture and/or the method for evaporating and drying the complex (1b) are generally similar to that given above in respect of complex (1a).

In yet another aspect, the present invention provides a method for the preparation of the ruthenium complex of formula (1c) as defined above, comprising the steps of:
(a) reacting [Ru (arene) Hal$_2$]$_2$ with the paracyclophane ligand of formula (2) in a solvent S; and
(b) reacting the product of step (a) with a ruthenium complex of formula (1a) in a solvent S to form the ruthenium complex of formula (1c).

The complex (1c) is prepared via a two-step reaction. Insofar as step (a) is concerned, the [Ru (arene) Hal$_2$]$_2$ may be [Ru (benzene) Hal$_2$]$_2$ or [Ru (toluene) Hal$_2$]$_2$, preferably Ru (benzene) Cl$_2$]$_2$. In one embodiment, the solvent S is preferably dimethylformamide.

The molar ratio of the [Ru (arene) Hal$_2$]$_2$:paracyclophane (2), the order in which the [Ru (arene) Hal$_2$]$_2$, paracyclophane (2) and solvent S are combined and/or the method for heating are generally similar to that discussed above with regard to the complex of formula (1a).

After a suitable time, a complex of formula (1a) is added to the reaction mixture and the reaction stirred and heated further. The solution of complex (1c) in the solvent S may then be used directly or the solvent S may be evaporated and the complex (1c) dried and, if desired, crystallised/recrystallised in the manner described above in respect of complex (1a). In one embodiment, the solvent/anti-solvent combination comprises DCM/hexane.

In another aspect, the present invention provides a process for the preparation of the ruthenium complex of formula (1d) as defined above, comprising the step of reacting polymeric [Ru Hal$_2$ (CO)$_2$]$_n$ with the paracyclophane ligand of formula (2) in the solvent S to form the complex of formula (1d).

The preferred polymeric [Ru Hal$_2$ (CO)$_2$]$_n$, molar ratio of the ruthenium starting material:paracyclophane (2), the order in which the ruthenium starting material, paracyclophane (2) and solvent S are combined, the method for heating, the method for evaporating and/or drying the complex (1d) are generally similar to that discussed above with regard to the complex of formula (1a).

It is preferred that all steps in the preparation and isolation of the complexes of formulae (1a), (1b), (1c) and (1d) are conducted under an inert atmosphere (e.g. nitrogen or argon).

The ruthenium complexes of formula (1a), (1b), (1c) or (1d) are useful in a variety of chemical transformations, such as isomerisation, hydrogenation, transfer hydrogenation, hydroformylation or carbonylation reactions.

The invention will be further illustrated by reference to the following non-limiting examples.

EXAMPLES

All preparations in the presence of the paracyclophane ligand (2) were carried out under inert conditions using high purity nitrogen or argon.

Example 1

[Ru Cl$_2$ (S)-Phanephos CO] Dimers

Polymeric [RuCl$_2$ CO (H$_2$O)]$_n$ was prepared according to Colton R., Farthing R, Aust. J. Chem. 1971, 24, 903:

To 1.62 ml of an hydrochloric solution of RuCl$_3$ (Ru metal assay 19.23 wgt %, 5 mmol RuCl$_3$) was added 20 ml of 37% hydrochloric acid and 20 ml of >98% formic acid and the dark red solution heated to reflux (oil bath at 135° C.) until the colour changed to green. This solution was evaporated at 10 mbar and heated to 60-70° C. A black crystalline solid containing polymeric [RuCl$_2$ CO (H$_2$O)]$_n$ was obtained.

350 mg of the black crystalline solid was dissolved in 5 ml of MeOH. To the solution was added 577 mg of (S)-Phanephos (1 mmol) in 15 ml of dichloromethane. The initially green mixture turned quickly yellow and the solvents were evaporated and the yellow residue dried at 5 mbar, 40° C. for 1 hour. By $^{31}$P{$^1$H} NMR (in CDCl$_3$) [Ru Cl$_2$ (S)-Phanephos CO] dimers were observed: 38.6 ppm (d), 8.0 ppm (d), and 32.5 ppm (d), 21.2 ppm (d).

Example 2

[Ru Cl$_2$ (R)-Xyl-Phanephos CO] Dimers 175 mg of the black crystalline solid containing polymeric [RuCl$_2$ CO (H$_2$O)]$_n$ of Example 1 was dissolved in 3 ml of MeOH. To the solution was added 345 mg of (R)-Xyl-Phanephos (0.5 mmol) in 15 ml of dichloromethane. The initially green mixture turned quickly yellow. The solvents were evaporated and the yellow residue dried at 5 mbar, 40° C. for 1 hour. By $^{31}$P{$^1$H} NMR (in CDCl$_3$) [Ru Cl$_2$ (R)-Xyl-Phanephos CO] dimers were observed: 38.9 ppm (d), 7.5 ppm (d) and 32.3 ppm (d), 21.0 ppm (d).

Example 3

[Ru Cl$_2$ (R)-Xyl-Phanephos CO DMF1] Complex

Polymeric [RuCl$_2$ (CO)$_2$)]$_n$ was prepared according to Colton R., Farthing R, Aust. J. Chem. 1971, 24, 903:

To 1.62 ml of an hydrochloric solution of RuCl$_3$ (Ru metal assay 19.23 wgt %, 5 mmol RuCl$_3$) was added 20 ml of 37% hydrochloric acid and 20 ml of >98% formic acid and the dark red solution heated to reflux (oil bath at 135° C.) until the colour changed to green and then orange. This solution was evaporated at 10 mbar and heated to 60-70° C. Polymeric [RuCl$_2$ (CO)$_2$)]$_n$ was obtained as a bright orange crystalline solid.

114 mg of [RuCl$_2$ (CO)$_2$)]$_n$ was combined with 345 mg of (R)-Xyl-Phanephos (0.5 mmol) and 15 ml of DMF. The mixture was heated in an oil bath at 116° C. for 120 minutes and small quantities of DMF stripped every 20 minutes. The DMF was then evaporated at 116° C. and 40 mbar and the residue dried. In addition to the [RuCl$_2$ (R)-Xyl-Phanephos CO DMF] complex with $^{31}$P{$^1$H} NMR resonances at 39.0 ppm (d) and 36.25 ppm (d), another isomer of [RuCl$_2$ CO (R)-Xyl-Phanephos DMF] with $^{31}$P{$^1$} NMR resonances at 43.1 ppm (d), 38.0 ppm (d) was obtained.

Example 4

[Ru Cl$_2$ (S)-Phanephos CO DMF] Complex

[RuCl$_2$ (CO)$_3$]$_2$ was prepared according to Colton R., Farthing R, Aust. J. Chem. 1971, 24, 903:

To 1.62 ml of an hydrochloric solution of RuCl$_3$ (Ru metal assay 19.23 wgt %, 5 mmol RuCl$_3$) was added 20 ml of 37% hydrochloric acid and 20 ml of >98% formic acid and the dark red solution heated to reflux (oil bath at 135° C.) until the colour changed to green, then orange and finally pale yellow. This solution was evaporated at 10 mbar and heating to 60-70° C. Pale yellow [RuCl$_2$ (CO)$_3$)]$_2$ was obtained as a crystalline solid.

256 mg of [RuCl$_2$ (CO)$_3$]$_2$ as obtained above was added as a solid to a solution of 577 mg of (S)-Phanephos (1 mmol) in 15 ml of DMF. The mixture was heated in an oil bath at 116° C. for 120 minutes. Then approximately 1 ml of DMF was stripped and a small sample of the solution added to CDCl$_3$ in an NMR tube. The assay of this sample gave a mixture containing [Ru Cl$_2$ (S)-Phanephos CO] dimers with $^{31}$P{$^1$H} NMR resonances at 38.6 ppm (d), 8.0 ppm (d) and 32.5 ppm (d), 21.2 ppm (d) and one [RuCl$_2$ (S)-Phanephos CO DMF] complex isomer with $^{31}$P{$^1$H} NMR resonances at 39.8 ppm (d) and 36.7 ppm (d).

The solution in DMF is further heated for seven hours, with approx 1 ml of DMF stripped every 2 hours. The solution was then cooled to room temperature and the DMF evaporated at 5 mbar, 60° C. and the yellow residue dried for 1 hour. The product was analysed by $^{31}$P{$^1$H} NMR in CDCl$_3$ and shown to be the [RuCl$_2$ (S)-Phanephos CO DMF] complex isomer with $^{31}$P{$^1$H} NMR resonances at 39.8 ppm (d) and 36.7 ppm (d).

The same product was obtained when 228 mg of [RuCl$_2$ (CO)$_2$)]$_n$ was heated with 577 mg of (S)-Phanephos (1 mmol) in 15 ml of DMF in an oil bath at 116° C. for two hours and then stripped. During the initial 30 minutes of the reaction, a compound consistent with a [RuCl$_2$ (S)-Phanephos (CO)$_2$] isomer {$^{31}$P{$^1$H} NMR in CDCl$_3$ 13.5 ppm (s)} was observed.

Example 5

[Ru Cl$_2$ (S)-Phanephos CO DMF] Complex 1.154 g of (S)-Phanephos (2 mmol) and 0.5 g (1 mmol) of [Ru(benzene)Cl$_2$]$_2$ were combined in a 80 mL Schlenk flask and mixed with 20 ml of dimethylformamide (DMF). The mixture was vigorously stirred and heated to 120° C. (oil bath). After 19 hours the reaction mixture was cooled and the clear red solution was concentrated by distillation using a rotary evaporator (60° C., 20-30 mbar). The brown residue was dried (60° C., 5 mbar) for 30 minutes. A $^{31}$P{$^1$H} NMR analysis of the dry product in CDCl$_3$ gave 80% of a [RuCl$_2$ (S)-Phanephos CO DMF] complex with resonances of 39.8 ppm (d) and 36.7 ppm (d) and a 20% of a second compound with resonances of 41.1 ppm (d), 29.4 ppm (d).

Upon recrystallisation from dichloromethane and hexane a mixture of isomers of [RuCl$_2$ CO (S)-Phanephos DMF] with $^{31}$P{$^1$H} NMR resonances at 42.1 ppm (d), 37.5 ppm (d), 41.8 ppm (d), 36.0 ppm (d), 39.8 ppm (d), 36.7 ppm (d) were obtained and the second compound with shifts of 41.1 ppm (d), 29.4 ppm (d) disappeared.

Example 6

[Ru Cl$_2$ (R)-Xyl-Phanephos CO DMF] Complex 660 mg (0.958 mmol) of (R)-Xyl-Phanephos and 228 mg (0.456 mmol) of [Ru(benzene)Cl$_2$]$_2$ were combined in a 50 ml Schlenk flask and mixed with 10 ml of dimethylformamide (DMF). The mixture was vigorously stirred and heated to 110° C. (oil bath). After 17 hours the reaction mixture was cooled and the clear red solution concentrated by distillation using a rotary evaporator (70° C., 20-30 mbar). The brown residue was dried (70° C., 5 mbar) for 30 minutes. $^{31}$P{$^1$H} NMR analysis of the dry product in CDCl$_3$ showed the formation of [RuCl$_2$ (R)-Xyl-Phanephos CO DMF] with $^{31}$P{$^1$H} NMR (in CDCl$_3$) shifts of 39.0 ppm (d) and 36.25 ppm (d).

Addition of 15 ml of methyl tert-butyl ether (MTBE) and 30 ml of hexane to a solution of the crude product in 5 ml of dichloromethane (DCM) at 0° C. yielded a precipitate that was isolated by filtration and dried. The purified product showed $^{31}$P{$^1$} NMR (in CDCl$_3$ shifts) of 39.0 ppm (d) and 36.25 ppm (d) and had IR absorptions at 1947 cm$^{-1}$ (CO) and 1674 (CHO, coordinated DMF).

Example 7

[Ru Cl$_2$ (R)-Xyl-Phanephos CO DMF] Complex

Example 6 was repeated starting from 2.89 g (4 mmol) of (R)-Xyl-Phanephos and 1.0 g (2 mmol) of [Ru(benzene)Cl$_2$]$_2$ in a 250 ml Schlenk flask using 40 mL of dimethylformamide (DMF). The product obtained after crystallisation from MTBE/DCM/hexane was analysed by $^{31}$P{$^1$H} NMR analysis in CDCl$_3$. A mixture containing 90% of the [RuCl$_2$ (R)-Xyl-Phanephos CO DMF] complex with shifts of 39.0 ppm (d) and 36.25 ppm (d) and 10% of a second isomer with shifts of 42.7 ppm (d), 29.8 ppm (d) were obtained.

Single crystal X-Ray diffraction of a crystal species obtained from a toluene/ethyl acetate solution showed that the main compound had the structure shown.

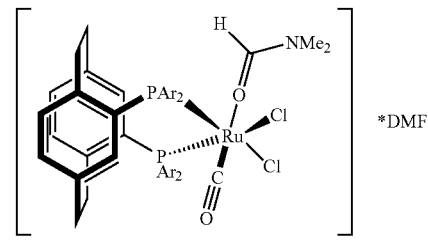

The retained crystals were dissolved in CDCl$_3$ and analysed by $^{31}$P{$^1$} NMR and shown to have the resonances of the major [RuCl$_2$ (R)-Xyl-Phanephos CO DMF] complex with shifts of 39.0 ppm (d) and 36.25 ppm. In addition, there was 10% of another isomer of [RuCl$_2$ CO (R)-Xyl-Phanephos DMF] with $^{31}$P{$^1$H} NMR resonances at 43.1 ppm (d), 38.0 ppm (d).

Example 8

[Ru S(S)-Phanephos Co] μ Cl$_3$ [Ru Cl (S)-Phanephos]

577 mg of (S)-Phanephos (1 mmol) and 250 mg (0.5 mmol) of [Ru(benzene)Cl$_2$]$_2$ were combined in a 80 ml Schlenk flask and mixed with 20 ml of dimethylformamide (DMF). The mixture was vigorously stirred and heated to 100° C. (oil bath) for 4 hours. To this solution was added 920 mg of the product mixture obtained in Example 5. The solution was stirred for further 10 minutes 100° C. (oil bath) and then the DMF was evaporated at 5 mbar, 60° C. A beige solid was obtained, which was recrystallised twice from dichloromethane/hexane.

Different from the [RuCl$_2$ (S)-Phanephos CO DMF] complexes obtained in Example 5, the $^{31}$P{$^1$H} NMR in CDCl$_3$ of the products was unchanged with resonances at 39.9 ppm (d), 36.9 ppm (d) and 39.0 ppm (d), 36.4 ppm (d). The stripped dichloromethane/hexane mother liquors contained the same compound. Solutions of the product in dichloromethane and CDCl$_3$ were heated for 15 hours at 40° C. without change. The monocarbonyl dimer [Ru (S)-Phanephos CO] μ Cl$_3$ [RuCl (S)-Phanephos] was obtained.

The invention claimed is:

1. A ruthenium complex of formula (1a), (1b), (1c) or (1d):

[Ru Hal$_2$ L CO S]     (1a)

[Ru$_2$ Hal$_4$ L$_2$ (CO)$_2$]     (1b)

[Ru$_2$ Hal$_4$ L$_2$ CO]     (1c)

[Ru Hal$_2$ L (CO)$_2$]     (1d)

wherein:
Hal is a halogen ligand,
L is a substituted or unsubstituted paracyclophane ligand of formula (2):

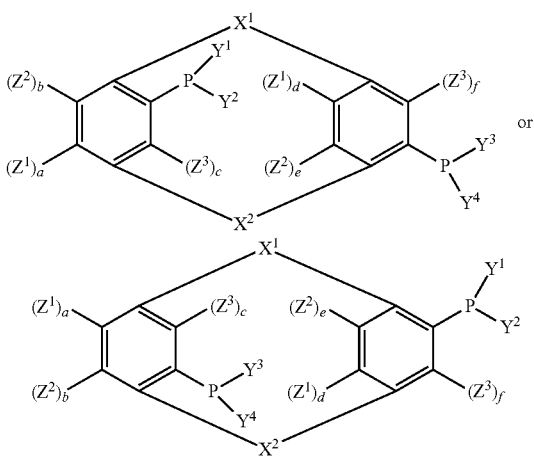

(2)

wherein X$^1$ and X$^2$ are linking groups comprising between 2 to 4 carbon atoms,
each Y$^1$, Y$^2$, Y$^3$ and Y$^4$ are independently selected from the group consisting of substituted or unsubstituted alkyl, substituted or unsubstituted cycloalkyl, substituted or unsubstituted aryl and substituted or unsubstituted heteroaryl,
each Z$^1$, Z$^2$ and Z$^3$ are the same or different and are substituting groups that optionally contain functional groups,
a, b, c, d, e and f are the integers 0 or 1 and a+b+c+d+e+f=0 to 6;
CO is a carbonyl ligand; and
S is a solvent ligand.

2. A ruthenium complex according to claim 1 wherein X$^1$ and X$^2$ are both —C$_2$H$_4$—.

3. A ruthenium complex according to claim 1, wherein each Y$^1$, Y$^2$, Y$^3$ and Y$^4$ are independently selected from the group consisting of methyl, ethyl, propyl, iso-propyl, butyl, iso-butyl, sec-butyl, tert-butyl, phenyl, naphthyl, anthracyl, 4-methylphenyl, 3,5-dimethylphenyl, 4-methoxyphenyl, 4-methoxy-3,5-dimethylphenyl, 4-methoxy-3,5-diisopropylphenyl, 4-methoxy-3,5-ditertbutylphenyl, 3,5-diisopropylphenyl, 3,5-ditertbutylphenyl, 4-dimethylamino-3,5-dimethylphenyl, 4-dimethylamino-3,5-diisopropylphenyl, 4-dimethylamino-3,5-ditertbutylphenyl and fluorenyl.

4. A ruthenium complex according to claim 1, wherein Z$^1$, Z$^2$ and Z$^3$ are independently substituting groups selected from C$_1$-C$_{30}$ branched or linear alkyl or phenyl, naphthyl or anthracyl groups.

5. A ruthenium complex according to claim 1 wherein Z$^1$, Z$^2$ or Z$^3$ are independently substituting groups comprising one or more functional groups selected from halide, hydroxyl, alkoxy, silyloxy, aralkyloxy, carbonyl, carboxyl, anhydride, methacryl, epoxide, vinyl, nitrile, nitro, sulphate, sulphonyl, mercapto, sulphide, amino, amine, imine, amide and imide.

6. A ruthenium complex according to claim 1, wherein a+b+c+d+e+f=1 or 2.

7. A ruthenium complex according to claim 1, wherein a+b+c=1 and/or d+e+f=1.

8. A ruthenium complex according to claim 1, wherein a+b+c+d+e+f=0.

9. A ruthenium complex according to claim 1, wherein S is a solvent ligand selected from the group consisting of amides, N-heterocyles, ketones, alcohols, esters, aromatic solvents, chlorinated alkanes, formic acid, dimethylsulfoxide and acetonitrile.

10. A ruthenium complex according to claim 1, wherein the complex of formula (1a) is a solid and further comprises a co-crystallised solvent.

11. A method for the preparation of a ruthenium complex of formula (1a) according to claim 1, comprising the step of:
(a) reacting polymeric [Ru Hal$_2$ (CO)$_2$]$_n$ or [Ru Hal$_2$ (CO)$_3$]$_2$ with a paracyclophane ligand of formula (2) in a solvent S to form the complex of formula (1a); or
(b) heating a complex of formula (1b) in a solvent S to form the complex of formula (1a); or
(c) reacting [Ru (arene) Hal$_2$]$_2$ with a paracyclophane ligand of formula (2) in a solvent S to form the complex of formula (1a), wherein at least a portion of the solvent S decarbonylates to form CO.

12. A method for the preparation of the ruthenium complex of formula (1b) according to claim 1, comprising the step of reacting polymeric [Ru (Hal)$_2$ CO (H$_2$O)]$_n$ with a paracyclophane ligand of formula (2) in a solvent mixture comprising at least one alcohol and chlorinated alkane to form the complex of formula (1b).

13. A method for the preparation of the ruthenium complex of formula (1c) according to claim 1, comprising the steps of:

(a) reacting [Ru (arene) Hal$_2$]$_2$ with a paracyclophane ligand of formula (2) in a solvent S; and
(b) reacting the product of step (a) with a ruthenium complex of formula (1a) in a solvent S to form the ruthenium complex of formula (1c).

14. A method for the preparation of the ruthenium complex of formula (1d) according to claim 1, comprising the step of reacting polymeric [Ru Hal$_2$ (CO)$_2$]$_n$ with a paracyclophane ligand of formula (2) in a solvent S to form the complex of formula (1d).

15. A method for performing isomerisation, hydrogenation, transfer hydrogenation, hydroformylation or carbonylation reactions, comprising utilizing a ruthenium complex according to claim 1 as a catalyst for said reactions.

16. A ruthenium complex according to claim 2, wherein $Z^1$, $Z^2$ and $Z^3$ are independently substituting groups selected from $C_1$-$C_{30}$ branched or linear alkyl or phenyl, naphthyl or anthracyl groups.

17. A ruthenium complex according to claim 2 wherein $Z^1$, $Z^2$ or $Z^3$ are independently substituting groups comprising one or more functional groups selected from halide, hydroxyl, alkoxy, silyloxy, aralkyloxy, carbonyl, carboxyl, anhydride, methacryl, epoxide, vinyl, nitrile, nitro, sulphate, sulphonyl, mercapto, sulphide, amino, amine, imine, amide and imide.

18. A ruthenium complex according to claim 2, wherein a+b+c+d+e+f=1 or 2.

19. A ruthenium complex according to claim 2, wherein a+b+c=1 and/or d+e+f=1.

20. A ruthenium complex according to claim 2, wherein a+b+c+d+e+f=0.

* * * * *